US007200535B2

(12) United States Patent
Abraham-Fuchs et al.

(10) Patent No.: US 7,200,535 B2
(45) Date of Patent: Apr. 3, 2007

(54) QUALITY CONTROL IN DISEASE MANAGEMENT SERVICES

(75) Inventors: Klaus Abraham-Fuchs, Erlangen (DE); Johannes Bieger, München (DE); Eva Rumpel, Erlangen (DE); Kai-Uwe Schmidt, Erlangen (DE); Daniel Tietz, Spardorf (DE)

(73) Assignee: Siemens Aktiengesellschaft, München ( * ) Notice: Subject to any disclaimer, the term of this patent is extended or adjusted under 35 U.S.C. 154(b) by 760 days.

(21) Appl. No.: 10/228,140

(22) Filed: Aug. 27, 2002

(65) Prior Publication Data

US 2003/0055681 A1 Mar. 20, 2003

(30) Foreign Application Priority Data

Aug. 27, 2001 (DE) ................................ 101 41 832

(51) Int. Cl.
*G06G 7/48* (2006.01)

(52) U.S. Cl. ................................ 703/6; 702/108; 705/2

(58) Field of Classification Search .................... 703/6; 702/108; 705/2
See application file for complete search history.

(56) References Cited

U.S. PATENT DOCUMENTS

| | | | | |
|---|---|---|---|---|
| 5,301,105 | A | 4/1994 | Cummings, Jr. | |
| 5,899,925 | A * | 5/1999 | Ochs et al. | 607/5 |
| 6,011,830 | A * | 1/2000 | Sasin et al. | 379/10.03 |
| 6,073,085 | A * | 6/2000 | Wiley et al. | 702/118 |
| 6,978,244 | B2 * | 12/2005 | Rovinelli et al. | 705/2 |
| 2002/0072933 | A1 * | 6/2002 | Vonk et al. | 705/2 |
| 2002/0127525 | A1 * | 9/2002 | Arington et al. | 434/262 |

FOREIGN PATENT DOCUMENTS

| | | |
|---|---|---|
| DE | 196 51 334 | 6/1998 |
| EP | 0 661 847 A2 | 7/1995 |
| EP | 0 917 078 | 5/1999 |

OTHER PUBLICATIONS

Wood, Bill J.; "Software Risk Management for Medical Devices", Jan. 1999, www.devicelink.com/mddi/archive/99/01/013a.html.*
European Search Report.
European Search Report, Oct. 2004.

* cited by examiner

*Primary Examiner*—Paul Rodriguez
*Assistant Examiner*—Russ Guill
(74) *Attorney, Agent, or Firm*—Alexander J. Burke

(57) ABSTRACT

A quality control system in disease management services for the enlightenment, development and motivation of patients in conjunction with telemonitoring of critical body values and, resulting from this, early recognition of risk situations, wherein random generators are used to create a virtual patient from the admissible patient data, wherein a random selection is made from the available hardware components, and wherein, likewise randomly generated, a random event is selected from a list of possible events in the disease management process, the system reaction when this event is run through being assessed by an expert system by using the reference responses known to the system in order to trace errors.

20 Claims, 1 Drawing Sheet

QUALITY CONTROL IN DISEASE MANAGEMENT SERVICES

FIELD OF THE INVENTION

The invention relates to a quality control system in disease management services for the enlightenment, development and motivation of patients in conjunction with telemonitoring of critical body values and, resulting from this, early detection of risk situations.

BACKGROUND OF THE INVENTION

Disease management services providers typically care for patients who suffer from a chronic common disease, such as diabetes, asthma or hypertension. Therefore, large numbers of patients are cared for with a largely standardized treatment plan over long time periods, typically months or years, which leads to a cost efficiency which is increased considerably as compared with traditional patient care.

Effective cost efficiency is achieved inter alia by the greatest possible automation of the patient care. For example, patient information material is automatically dispatched at fixed intervals or consultancy calls are carried out, or measured values, for example blood pressure, are sent in digital form by the patient to the control center, are automatically assessed there and, if limiting values are violated, notifications with an appropriate recommendation for treatment are sent automatically by fax or e-mail to the relevant doctor or the patient.

As in the case of all highly automated processes, systematic quality control of this telemedical disease management process is necessary here too in order to avoid errors or to discover them in good time. Possible error sources range from defective cables or computers via wrongly entered telephone numbers up to falsification or loss in the case of digital data transmission.

EP 0 917 078 A1 discloses a disease management system, but no monitoring of the function of this system is provided there.

DE 196 51 334 A1 describes an operational test method and a device suitable for this in order to carry out an operational test for a testing system. There, however, it is not the real system itself but only a test system which is run through, so that the errors which occur in practice in the disease management service system cannot in particular be detected with such a test system.

SUMMARY OF THE INVENTION

The invention is therefore based on the object of providing a quality control system which permits errors in the extremely wide range of areas and stages of such a disease management service to be discovered and to be corrected automatically.

In order to achieve this object, the invention provides that random generators are used to create a virtual patient from the admissible patient data, that a random selection is made from the available hardware components, and that, likewise randomly generated, a random event is selected from a list of possible events in the disease management process, the system reaction when this event is run through being assessed by an expert system by using the reference responses known to said system in order to trace errors.

The quality control system according to the invention resembles the quality testing of software with complex user interfaces. There, use is made to some extent of test software which is based on the principle of the statistical simulation of possible real operating sequences: in branched input trees, a start is made in an arbitrary and randomly distributed manner with an arbitrary input value. At the next branching level, this input leads to new options for possible input, for which again an (admissible) input value is selected randomly. In this way, the system can be run through in any desired scenarios, in particular also in scenarios which are rare under real conditions, and can be checked for stability and error messages. According to the invention, this test concept is transferred to disease management services. Since, as opposed to software which is produced once and freed of errors, errors can reoccur continually in disease management services, here a functional test has to be carried out continuously over the entire operating time period, for which reason test runs of this type should be run through automatically with virtual patients at predefined time intervals.

The admissible patient data, for example date of birth, basic illness, measured values specified by the doctor to be monitored, family doctor providing care, and so on, the admissible hardware components—a patient's own computer, fax machines, telephone links, servers and so on, and a list of possible events in the disease management process, for example expiry date for a specific informative text, a patient calling the call center about a specific type of complaint, electronically transmitted blood pressure value and so on should, in a development of the invention, be stored in separate databases.

In order at the same time to be able to take increased account also of real errors which have occurred earlier and not to generate a random test run just randomly generated from lists of all conceivable events and personal data or hardware components, in a refinement of the invention, provision can also be made that, in addition to the randomly generated selection of events, real cases from the past and/or real errors from the past and/or real or fictitious cases put together by specialist experts are run through regularly or in a randomly generated manner.

The notifications from the system should in this case be identified as test queries, depending on their significance, in order that an emergency doctor is not sent to this patient merely on the basis of a test which has been run through using a virtual patient. The result of the test should definitely merely be whether the query and the hardware components involved in the query, that is to say the technical transmission devices and so on, actually function and whether—which is likewise of importance for the function of the quality control system according to the invention—possible human error sources also need to be ruled out. For this purpose, in addition to checking technical functions, in particular therefore the hardware components already mentioned, checking and assessment of possible human error sources, such as reaction time to notifications or the like, should also be carried out. This is because if there is no or no timely reaction from the patient, a doctor or another system element, then it may be necessary to check whether the relevant doctor can continue to be incorporated into the disease management service system or, possibly, must be ruled out because of unreliability and replaced by another doctor.

The test runs and results should be stored for an assessment of business segments or the like; in every case, the assessment system should be provided with a reporting system which, when required, informs or interrogates engineers, doctors or a person responsible for quality.

BRIEF DESCRIPTION OF THE DRAWINGS

Further advantages, features and details of the invention emerge from the following description of some exemplary embodiments and by using the drawing, which shows a flowchart of the quality control system according to the invention.

DETAILED DESCRIPTION OF THE INVENTION

Figure 1:
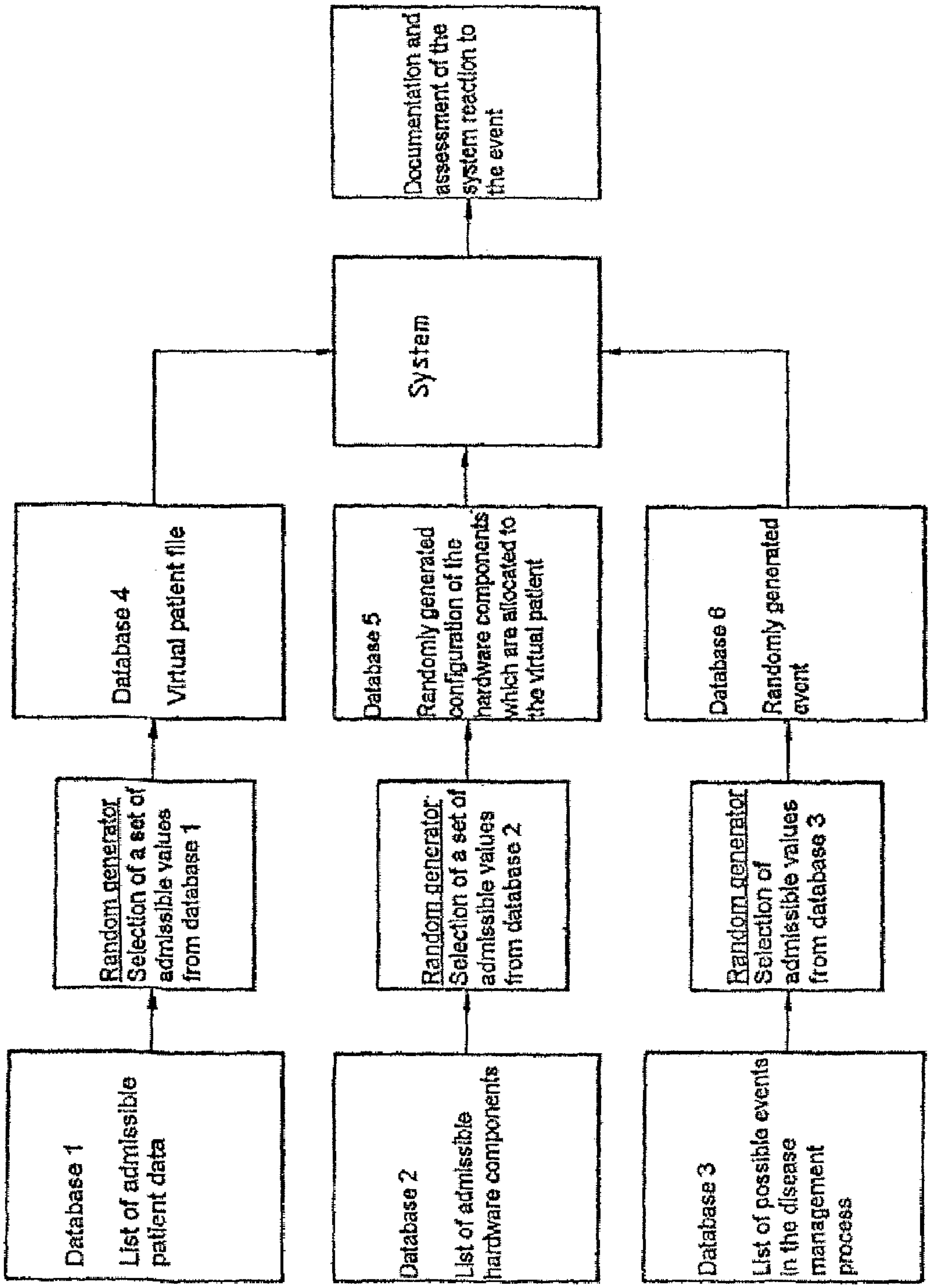

Stored in three databases are lists, firstly of admissible patient data, secondly of admissible hardware components and thirdly of possible events in the disease management process, from which in each case a random generator selects a set of admissible values and supplies it to further databases 4 to 6. Via a randomly generated configuration of the hardware components, the randomly generated possible event in the disease management system taken from the database 3 by the random generator is assigned to the virtual patient, and the system reaction when this event is run through is documented and assessed. In detail, this can be carried out, for example, as described below:

These requirements are met by the invention in the following way:

- A "virtual patient" is created in the patient card index of the disease management service provider. All the "statistical" (that is to say characteristic and unchangeable for this patient) information units (e.g. date of birth, basic illness, measured values specified by the doctor to be monitored, family doctor providing care) from this patient file are selected by a random generator from a list of admissible values.
- A further file allocates this "virtual patient file" a network of hardware components, which are needed to care for this patient (for example fax number 25, Call Center Hamburg North, server number 32, back-up computer number 8), again selected by random generator from a list of realy existing and admissible hardware components.
- A third file contains information elements relating to possible events in the disease management process (expiry date for informative text number 3; call from the patient to the call center: "I have acute breathing difficulties"; electronically transmitted blood pressure value etc.). In addition, the type of event and values associated with the event (blood pressure 90/180) are selected by random generator.

Such a type of random configuration of patient data, hardware configuration and event can be regenerated as frequently as desired (hourly, daily, weekly).

The occurrence of the randomly generated "event" then triggers a system reaction (against the background of likewise randomly generated basic patient data and within the network of the randomly generated hardware configuration).

EXAMPLES

- the randomly generated blood pressure value exceeds an admissible limiting value and automatically triggers an e-mail or a fax notification to the doctor providing care, this notification preferably being identified as a test query.
- the required information document is delivered to the "virtual patient".

To a certain extent, the triggered system reaction can also be merely simulated, in that instead of the postal delivery of an envelope, an e-mail is dispatched, whose arrival at the test computer is documented automatically, and therefore the entire quality checking process is completely digitally simulated, evaluated and documented, for example in such a way that: the randomly generated event XYZ has triggered the expected system reaction ACD within the time period of x hours under the boundary conditions a, b and c.

Other simulation scenarios also check, in addition to purely technical functions, possible human error sources (does the contracted doctor react to the notification fax within an appropriate time frame and with the expected action). If appropriate, such action of a human involved in the process can no longer be registered and documented completely automatically, but has to be accepted, assessed and documented by a person responsible for quality. The proposed system is therefore capable of checking and documenting virtually any desired process configurations within the entire disease management services (involved software, devices and humans) at any desired time intervals. In particular, with this the process reaction to the emergency situations which are particularly rare in reality, such as the occurrence of a cardiac infarction, delirium at extremely high blood sugar values, and so on, can also be checked.

From this, a quality statistic can be derived which can quantify and represent failure rates, erroneous reactions and so on with a statistically relevant meaningfulness. Thus, with the aid of such a statistic, for example the positive action of a change in the process (for example replacement of faulty fax machines by a new product generation in subsidiary X, changing the e-mail provider, and so on) or comparisons between business segments (caring for the patients in the conurbation of cities X and Y) can also be quantified and documented.

For the purpose of even better understanding of the invention, a practical exemplary embodiment of a random configuration of a virtual patient will be described below:

A patient with the virtual name Peter Müller suffers from diabetes type II. The patient is assigned a blood-sugar measuring instrument which can be read digitally, with the stipulation that blood sugar be measured at least five times per day. The measured values are sent by e-mail, using the virtual sender address peter.müller@t-online.de, to a central server and are automatically assessed there using an upper and lower threshold value rule. If these threshold values are violated, a fax is automatically sent to the family doctor, Herr Meier, responsible for Herr Müller within the disease management service, with the request to contact Herr Müller without delay and to ensure that necessary medical measures are initiated (for example insulin injection in the event of hyperglycemia). The stipulation for the family doctor is firstly to reach Herr Müller by telephone in order to check whether Herr Müller can himself handle the situation. If he cannot reach Herr Müller, then an emergency doctor must be sent to Herr Müller without delay, since it must be assumed that Herr Müller has suffered hyperglycemic shock.

In the virtually constructed case example, the blood sugar value is generated randomly by the quality assurance program, in the present case at 220 mg/dl (hyperglycemia). The value is downloaded to the central server from the virtual e-mail sender peter.müller@t-online.de.

The system components which are involved in this virtual patient and which are checked in interaction in this case, are therefore:

- e-mail arrival at the central server
- evaluation software in the central server
- fax sender from the central server to Dr. Meier's practice
- reaction of the family doctor Herr Meier telephone link between the doctor's practice and the test computer.

If the call from the family doctor arrives at the test computer within a predefined time, for example five minutes (by which the family doctor is informed by means of an automatic statement that this is a test case for quality assurance), then the system documents the test case and the proper functioning of all the components involved. If the call does not arrive, then the virtual error case is passed on to the service personnel, who then have to trace the faulty link in the system chain by means of the system log, etc. and rectify the fault.

The invention claimed is:

1. A quality control system in disease management services for early recognition of system-related risk situations comprising:

a data processor, said data processor including, a patient data generator for automatically selecting data representative of a test patient based on known patient data;

a hardware component generator for automatically selecting at least one hardware component needed for providing care to said test patient, and an event generator for automatically selecting a test event from a list of possible events in a disease management process and associating said selected event with said test patient, said system automatically processes said selected event and assesses a response to said selected event by using reference responses known to said system, said system tracing system operation errors and determining a risk value associated with an existence of a system-related risk and communicating data representing said risk value to a third party.

2. The quality control system as claimed in claim 1, wherein said known patient data, said hardware components and said list of possible events in the disease management process are stored in separate databases.

3. The quality control system as claimed in claim 1, wherein said selected event includes at least one, of (a) data representing a prior actual patient event, (b) data representing prior actual system errors, and (c) a combination of data representing a prior actual patient event and a test event for processing by said system.

4. The quality control system as claimed in claim 1, wherein said system automatically processes and assesses said selected event at predefined time intervals.

5. The quality control system as claimed in claim 1, wherein said system identifies said response as a rest query and notifies a caregiver of said test query.

6. The quality control system as claimed in claim 1, wherein said response assesses at least one of (a) technical functions of said selected hardware components, and (b) a source of human error including reaction time to a response notification.

7. The quality control system as claimed in claim 1, wherein said response is stored for later.

8. The quality control system as claimed in claim 1, further informing arid querying at least one engineers, doctors and a person responsible for quality about system operation.

9. A method for early recognition of system-related risk situations in a quality control system in disease management services comprising the activities of:

automatically selecting data representative of a test patient based on known patient data;

automatically selecting at least one hardware component needed for providing care to the test patient;

automatically selecting a test event from a list of possible events in die a disease management process and associating the selected event with the test patient; and automatically processing the selected event and assessing a response to the selected event by using reference responses known to the system for tracing system operation errors and determining a risk value associated with a system-related risk, and communicating data representing said risk value to a third party.

10. The method as claimed in claim 9, further comprising the activity of storing in separate databases the known patient data, the hardware components and the list of possible events in the disease management process.

11. The method as claimed in claim 9, wherein said activity of selecting a test event further comprises selecting at least one of (a) data representing a prior actual patient event, (b) data representing prior actual system errors, and (c) a combination of data representing a prior actual patient event and a test event for processing by an expert system.

12. The method as claimed in claim 9, wherein said activity of processing and assessing the test event occurs at predefined time intervals.

13. The method as claimed in claim 9, further comprising the activities of identifying the response as a test query, and notifying a caregiver of the test query.

14. The method as claimed in claim 9, wherein said activity of assessing the response to the test event further comprises assessing at least one of (a) technical functions of the selected hardware components, and (b) a source of human error including reaction time to a response notification.

15. The method as claimed in claim 9, further comprising the activity of storing the response for later evaluation.

16. The method as claimed in claim 9, further comprising the activity of reporting a quality of system operation to at least one of engineers, doctors and a person responsible for system operation quality.

17. The method as claimed in claim 9 wherein said activity of automatically selecting a test event further comprises selecting an event from at least one of a) expiration date for a specific informative text; b) a patient calling a call center about a specific type of complaint and c) an electronically transmitted physiological value.

18. The method as claimed in claim 9 wherein the activity of automatically selecting data representative of a test patient-based on known patient data further comprises selecting data representing at least one of (a) date of birth; (b) basic illness; (c) measured values specified by a doctor to be monitored and (d) family doctor providing care.

19. The quality control system as claimed in claim 1 wherein said list of possible events in the disease management process includes at least one of (a) expiration date for a specific informative text; (Ii) a patient calling a call center about a specific type of complaint and (c) an electronically transmitted physiological value.

20. The quality control system as claimed in claim 1 wherein said known patient data includes at least one of (a) date of birth; (b) basic illness; (c) measured values specified by a doctor to be monitored and (d) family doctor providing care.

* * * * *

UNITED STATES PATENT AND TRADEMARK OFFICE

CERTIFICATE OF CORRECTION

PATENT NO. : 7,200,535 B2
APPLICATION NO. : 10/228140
DATED : April 3, 2007
INVENTOR(S) : Klaus Abraham-Fuchs et al.

It is certified that error appears in the above-identified patent and that said Letters Patent is hereby corrected as shown below:

In the Claims: Col. 6, line 4 delete “die a” and replace with --a--

Signed and Sealed this

Fifth Day of June, 2007

JON W. DUDAS

*Director of the United States Patent and Trademark Office*